(12) United States Patent
O'Coin

(10) Patent No.: US 8,696,802 B2
(45) Date of Patent: Apr. 15, 2014

(54) HEAT EXCHANGER

(75) Inventor: James R. O'Coin, Somers, CT (US)

(73) Assignee: Hamilton Sunstrand Space Systems International, Inc., Windsor Locks, CT (US)

( * ) Notice: Subject to any disclaimer, the term of this patent is extended or adjusted under 35 U.S.C. 154(b) by 133 days.

(21) Appl. No.: 13/411,054

(22) Filed: Mar. 2, 2012

(65) Prior Publication Data

US 2013/0228317 A1    Sep. 5, 2013

(51) Int. Cl.
F28F 7/00    (2006.01)
B01D 53/02    (2006.01)

(52) U.S. Cl.
USPC ............ 96/146; 165/4; 165/10; 165/185; 95/115

(58) Field of Classification Search
None
See application file for complete search history.

(56) References Cited

U.S. PATENT DOCUMENTS

| 4,029,483 | A | * | 6/1977 | Long ........................ 95/139 |
| 5,281,254 | A |   | 1/1994 | Birbara et al. |
| 5,376,614 | A |   | 12/1994 | Birbara et al. |
| 5,454,968 | A |   | 10/1995 | Nalette et al. |
| 6,041,617 | A | * | 3/2000 | Sanada et al. .............. 62/480 |
| 6,102,107 | A | * | 8/2000 | Dunne ..................... 165/104.12 |
| 6,263,958 | B1 |   | 7/2001 | Fleishman |
| 6,601,404 | B1 |   | 8/2003 | Roderick |
| 6,973,963 | B2 | * | 12/2005 | Dunne et al. ............ 165/104.12 |
| 7,736,416 | B2 |   | 6/2010 | Nalette et al. |
| 8,322,408 | B2 | * | 12/2012 | Yoshioka et al. ............ 165/182 |
| 2009/0217691 | A1 |   | 9/2009 | Schmidt et al. |
| 2010/0024448 | A1 |   | 2/2010 | Critoph |
| 2011/0247494 | A1 | * | 10/2011 | Dinnage et al. ................. 95/92 |

FOREIGN PATENT DOCUMENTS

WO    9910091 A1    3/1999

* cited by examiner

Primary Examiner — Duane Smith
Assistant Examiner — Phillip Shao
(74) Attorney, Agent, or Firm — Cantor Colburn LLP

(57) ABSTRACT

A heat exchanger is provided and includes a frame defining a volumetric body with substantially flat upper and lower sides that each has inwardly extending ribs defining airflow pathways, heat exchange elements disposed within an interior of the body and partition walls disposed to run perpendicularly with respect to the ribs and to transmit loading between the upper and the lower sides from the ribs and through the interior of the body.

20 Claims, 3 Drawing Sheets

HEAT EXCHANGER

FEDERAL RESEARCH STATEMENT

This disclosure was developed in part in accordance with Navy contract N65540-11-C-0015. The government has certain rights to this invention

BACKGROUND OF THE INVENTION

The subject matter disclosed herein relates to a heat exchanger and to a heat exchanger assembly.

Sorbent canister heat exchangers may be employed in various applications including, but not limited to, air purifying systems for manned spacecraft and submarines. Such systems remove carbon dioxide from recirculated air so that the air can be re-used for onboard personnel without the need for refitting or repeated resurfacing (as the case may be). When in use, the sorbent canister heat exchangers flow a coolant about a sorbent material such that the sorbent material is maintained at a temperature at which the sorbent material absorbs and desorbs carbon dioxide.

Since space is at a premium on manned spacecraft and submarines, it is often necessary to design sorbent canister heat exchangers to be as small and compact as possible. In these cases, it is often seen that canisters with flat surfaces provide for the most compact design. However, when the canisters are exposed to external loading from, for example, depth charge shock waves or external pressure, the flat surfaces are prone to deformation that is transmitted to the relatively structurally weak heat exchange elements in the canister interiors. This leads to damage and possible failure of the canisters.

BRIEF DESCRIPTION OF THE INVENTION

According to one aspect of the invention, a heat exchanger is provided and includes a frame defining a volumetric body with substantially flat upper and lower sides that each has inwardly extending ribs defining airflow pathways, heat exchange elements disposed within an interior of the body and partition walls disposed to run perpendicularly with respect to the ribs and to transmit loading between the upper and the lower sides from the ribs and through the interior of the body.

According to another aspect of the invention, a heat exchanger is provided and includes a frame defining a volumetric body with substantially flat upper and lower sides that each has inwardly extending ribs defining airflow pathways, heat exchange elements disposed within the body and including a tubular element through which a first medium is directable and fins, the fins being oriented perpendicularly with respect to the ribs and the tubular element and partition walls disposed to run perpendicularly with respect to the ribs and to transmit loading between the upper and the lower sides from the ribs and through the interior of the body.

According to yet another aspect of the invention, a heat exchanger assembly including multiple heat exchangers is provided. Each heat exchanger includes a frame defining a substantially rectangular, volumetric body with substantially flat upper and lower sides that are each configured to register with a complementary side of an adjacent heat exchanger and have inwardly extending ribs defining airflow pathways, heat exchange elements disposed within the body and including a tubular element through which a first medium is directable and fins, the fins being oriented perpendicularly with respect to the ribs and the tubular element and partition walls disposed to run perpendicularly with respect to the ribs and to transmit loading between the upper and the lower sides from the ribs and through the interior of the volumetric body.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying figures in which:

The detailed description explains embodiments of the invention, together with advantages and features, by way of example with reference to the figures.

DETAILED DESCRIPTION OF THE INVENTION

Figure 1:
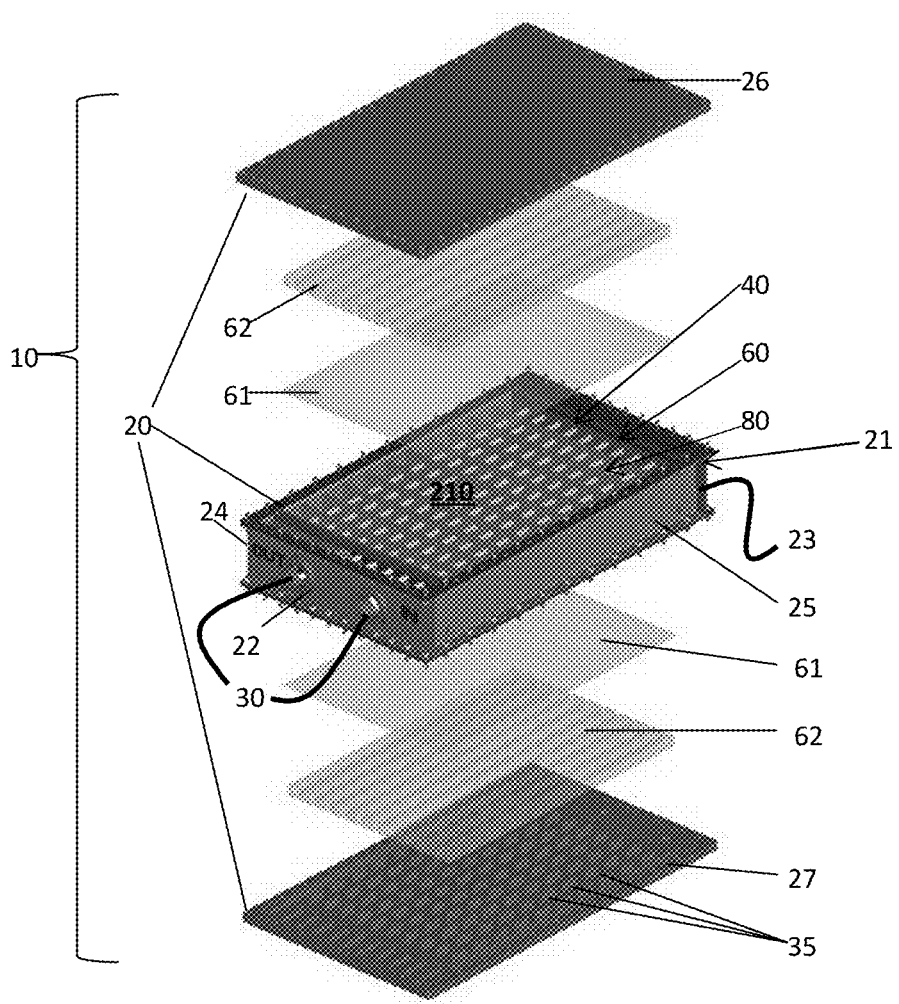
FIG. 1 is an exploded perspective view of a heat exchanger.
Figure 2:
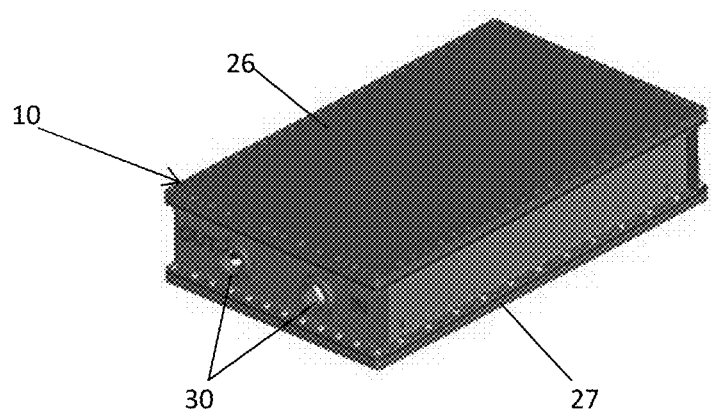
FIG. 2 is a perspective view of the heat exchanger of FIG. 1 as assembled.
Figure 3:
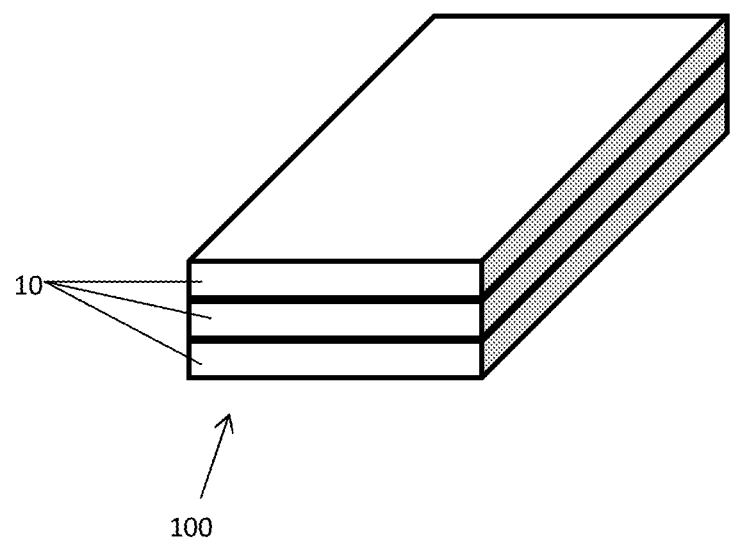
FIG. 3 is a perspective view of a heat exchanger assembly.

With reference to FIG. 1, an exploded view of a heat exchanger 10 is provided and with reference to FIG. 2, a perspective view of the heat exchanger 10 is provided. As shown in FIGS. 1 and 2, the heat exchanger 10 includes a frame 20, heat exchange elements 40, sorbent material 60 and structural partition walls 80. The frame 20 is formed to define a volumetric body 21 that may be substantially rectangular, for example, with longitudinal end faces 22 and 23, sidewalls 24 and 25 and substantially flat upper and lower sides 26 and 27. The end faces 22 and 23 and possibly the sidewalls 24 and 25 may be formed to define through-holes 30 by which air is permitted to enter an interior 210 of the volumetric body 21. With reference to FIG. 3, the heat exchanger 10 may be disposed in a heat exchanger assembly 100 in which multiple heat exchangers 10 are disposed in a substantially vertical column with complementary upper and lower sides 26 and 27 (FIG. 2) of adjacent heat exchangers 10 abutting one another.

Figure 4:
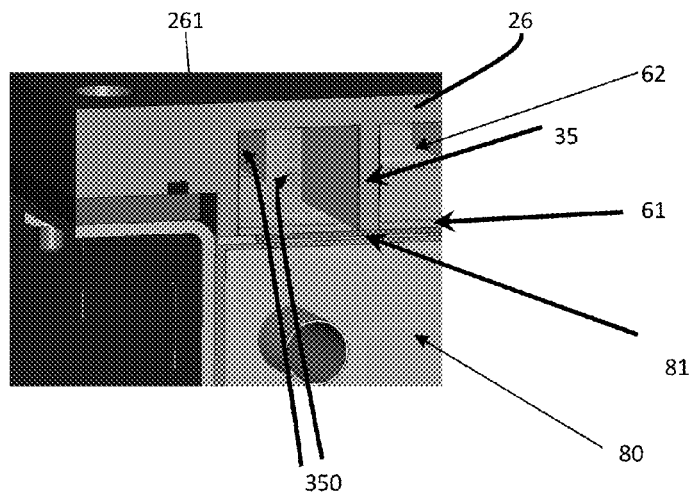
FIG. 4 is an enlarged perspective view of an interior of the heat exchanger of FIG. 1.

With reference to FIG. 4, the upper side 26 has a substantially flat exterior surface 261 and ribs 35. The ribs 35 are oriented substantially in parallel with a longitudinal axis of the volumetric body 21 (FIG. 1) as defined from end face 22 (FIG. 1) to end face 23 (FIG. 1). The ribs 35 extend inwardly toward the interior 210 (FIG. 1) of the volumetric body 21 (FIG. 1) and are disposed non-contiguously in order to define airflow pathways 350. Thus, air permitted to enter the interior 210 of the volumetric body 21 (FIG. 1) via the through-holes 30 (FIG. 1) may be distributed relatively evenly throughout the interior 210.

Figure 5:
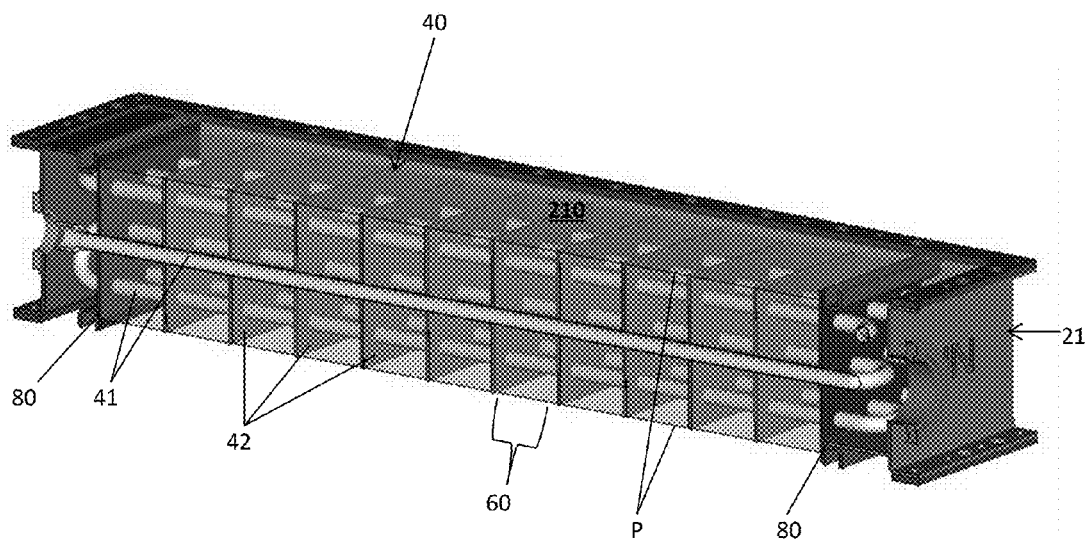
FIG. 5 is an enlarged perspective view of heat exchange elements of the heat exchanger of FIG. 1.

With reference to FIG. 5, the heat exchange elements 40 disposed within the interior 210 of the volumetric body 21 include a tubular element 41 and fins 42. The tubular element 41 may be disposed between the end faces 22 and 23 (FIG. 1) to run along the longitudinal axis through the interior 210 in a back and forth pattern via tube sections and hairpins. A first medium such as coolant fluid (i.e., water) may be directed to flow through the tubular element 41. The tubular element 41 may be a single, continuous part or multiple separate parts. The fins 42 are formed to define through-holes through which the tubular element 41 extends and are disposed to run perpendicularly with respect to the tubular element 41 and the ribs 35 (FIG. 1). Each fin 42 may be substantially thin and formed of a thermally conductive material such as metal or metallic alloy by which thermal conduction with respect to the first medium is achievable.

The sorbent material 60 may be provided in pellet form (not shown) and is disposed among the heat exchange elements 40 within the interior 210 of the volumetric body 21. More particularly, the sorbent material 60 may be provided between the fins 42 such that thermal conduction between the first medium, the fins 42 and the sorbent material 60 is facilitated. This thermal conduction serves to maintain a temperature of the sorbent material 60 within a given, predefined range at which the sorbent material 60 is able to relatively efficiently absorb gases from the air flowing through the airflow pathways 350 (FIG. 4).

With reference back to FIG. 1, the sorbent material 60 may be supported among the heat exchange elements 40 and within the interior 210 of the volumetric body 21 by upper and lower layers of structural features. The upper layers may include a retention screen 61 to retain the sorbent material 60 in vertical position and a structural foam layer 62 to provide structural support to the retention screen 61. Neither the retention screen 61 nor the structural foam layer 62 adds any appreciable obstruction to air flow throughout the interior 210. In accordance with embodiments, the structural foam layer 62 may be formed of multiple pieces without substantially sacrificing structural rigidity. In accordance with further embodiments, the multiple pieces may be aligned such that the ribs 35 extend in between the multiple pieces to offer positional constraint. The structural foam may be made from metals such as aluminum or copper or a non-metallic material such as carbon or silicon carbide.

As shown in FIG. 5, the structural partition walls 80 are disposed among and substantially in parallel with the fins 42 to run perpendicularly with respect to the ribs 35 (FIG. 1) and the tubular element 41. As with the fins 42, the partition walls 80 are formed to define through-holes through which the tubular element 41 extends. In accordance with embodiments, the partition walls 80 may be disposed in a longitudinal array through the interior 210 of the volumetric body 21 with uniform or non-uniform spacing from one another. Where the partition walls 80 are uniformly spaced from one another, a uniform number of fins 42 may be interposed between adjacent partition walls 80. Where the partition walls 80 are non-uniformly spaced from one another, a non-uniform number of fins 42 may be interposed between adjacent partition walls 80.

Still referring to FIG. 5, it is seen that the fins 42 have upper and lower edges that define upper and lower planes, P, and that the partition walls 80 protrude above and below the upper and lower planes, P, respectively. As such, when forces or external loads are applied to the upper and lower sides 26 and 27, the ribs 35 transmit force to the upper and lower layers of structural features as described above and to the partition walls 80 at contact points 81 (see FIG. 4) defined where the ribs 35 cross the partition walls 80. The transmitted force may be generated by an external load, such as pressure applied to either or both of the upper and lower sides 26 and 27 and, by transmitting such force or loading between the upper and lower sides 26 and 27 from the ribs 35 and through the interior 210 of the volumetric body 21, the partition walls 80 prevent the fins 42 from seeing or experiencing any forces or loads.

Where the forces or external loading is substantial and would crush the fins 42 if not for the partition walls 80, the partition walls 80 serve to protect the fins 42 from crushing effects and tend to increase a lifetime of the heat exchanger 10.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A heat exchanger, comprising:
a frame defining a volumetric body having a longitudinal axis with substantially flat upper and lower sides that each has inwardly extending ribs, each of the ribs being oriented substantially in parallel with the longitudinal axis and having a non-contiguous structure defined along the longitudinal axis that defines airflow pathways;
heat exchange elements disposed within an interior of the body; and
partition walls disposed to run perpendicularly with respect to the ribs and to transmit loading between the upper and the lower sides from the ribs and through the interior of the body.

2. The heat exchanger according to claim 1, wherein the body is substantially rectangular.

3. The heat exchanger according to claim 1, further comprising sorbent material disposed among the heat exchange elements within the interior of the body.

4. The heat exchanger according to claim 1, wherein sidewalls of the frame are formed to define through-holes for admitting airflow into the interior of the body.

5. The heat exchanger according to claim 1, further comprising:
retainer screens disposed at each of the upper and the lower sides of the heat exchange elements and sorbent material; and
structural foam layers to support the retainer screens at each of the upper and the lower sides of the heat exchange elements.

6. The heat exchanger according to claim 1, wherein the heat exchange elements comprise:
a tubular element through which coolant is directable; and
fins running perpendicularly with respect to the ribs.

7. The heat exchanger according to claim 6, wherein the partition walls are disposed among the fins.

8. The heat exchanger according to claim 1, wherein the heat exchange elements further comprise pellets of sorbent material.

9. A heat exchanger, comprising:
a frame defining a volumetric body having a longitudinal axis with substantially flat upper and lower sides that each has inwardly extending ribs, each of the ribs being oriented substantially in parallel with the longitudinal axis and having a non-contiguous structure defined along the longitudinal axis that defines airflow pathways;
heat exchange elements disposed within the body and including a tubular element through which a first medium is directable and fins, the fins being oriented perpendicularly with respect to the ribs and the tubular element; and partition walls disposed to run perpendicularly with respect to the ribs and to transmit loading between the upper and the lower sides from the ribs and through the interior of the body.

10. The heat exchanger according to claim 9, wherein the body is substantially rectangular.

11. The heat exchanger according to claim 9, further comprising sorbent material disposed among the heat exchange elements within the interior of the body.

12. The heat exchanger according to claim 11, wherein the sorbent material comprises a plurality of pellets.

13. The heat exchanger according to claim 9, wherein sidewalls of the frame are formed to define through-holes for admitting airflow into the interior of the body.

14. The heat exchanger according to claim 9, further comprising:
retainer screens disposed at upper and lower sides of the heat exchange elements and sorbent material; and
structural foam layers to support the retainer screens at the upper and the lower sides of the heat exchange elements.

15. The heat exchanger according to claim 9, wherein the partition walls are disposed among the fins.

16. A heat exchanger assembly including multiple heat exchangers that each comprise:
a frame defining a substantially rectangular, volumetric body having a longitudinal axis with substantially flat upper and lower sides that are each configured to register with a complementary side of an adjacent heat exchanger and that have inwardly extending ribs, each of the ribs being oriented substantially in parallel with the longitudinal axis and having a non-contiguous structure defined along the longitudinal axis that defines airflow pathways;
heat exchange elements disposed within the body and including a tubular element through which a first medium is directable and fins, the fins being oriented perpendicularly with respect to the ribs and the tubular element; and
partition walls disposed to run perpendicularly with respect to the ribs and to transmit loading between the upper and the lower sides from the ribs and through the interior of the volumetric body.

17. The heat exchanger according to claim 16, further comprising pellets of sorbent material disposed among the heat exchange elements.

18. The heat exchanger according to claim 16, wherein sidewalls of the frame are formed to define through-holes for admitting airflow into the interior of the volumetric body.

19. The heat exchanger according to claim 16, further comprising:
retainer screens disposed at upper and lower sides of the heat exchange elements and sorbent material; and
structural foam layers to support the retainer screens at the upper and the lower sides of the heat exchange elements.

20. The heat exchanger according to claim 16, wherein the partition walls are disposed among the fins.

* * * * *